United States Patent [19]

Van Driessche et al.

[11] Patent Number: 5,045,057
[45] Date of Patent: Sep. 3, 1991

[54] APPARATUS AND METHOD FOR WITHDRAWING AN OPTIMUM AMOUNT OF BLOOD PER UNIT OF TIME FROM A DONOR

[75] Inventors: Petrus J. D. M. Van Driessche, Jansteen; Lambertus G. P. Dalmolen, Arnhem, both of Netherlands

[73] Assignee: Akzo nv, Arnhem, Netherlands

[21] Appl. No.: 358,770

[22] Filed: May 30, 1989

[30] Foreign Application Priority Data

Jun. 1, 1988 [NL] Netherlands ............ 8801400

[51] Int. Cl.⁵ .............................. A61M 1/10
[52] U.S. Cl. .......................... 604/50; 604/66; 604/67
[58] Field of Search .......... 604/4, 6, 50, 67, 66; 128/670, 673; 364/413.02, 413.27; 340/537

[56] References Cited

U.S. PATENT DOCUMENTS

| | | | |
|---|---|---|---|
| 3,882,861 | 5/1975 | Kettering et al. | 128/214 |
| 3,946,731 | 3/1976 | Lichtenstein | 128/214 |
| 3,949,734 | 4/1976 | Edwards et al. | 128/1 |
| 4,086,924 | 5/1978 | Latham, Jr. | 128/214 |
| 4,285,464 | 8/1981 | Latham, Jr. | 604/6 X |
| 4,385,630 | 5/1983 | Gilcher et al. | 604/31 |
| 4,447,191 | 5/1984 | Bilstad et al. | 417/12 |
| 4,468,219 | 8/1984 | George et al. | 604/66 |
| 4,657,529 | 4/1987 | Prince et al. | 604/6 |
| 4,688,577 | 8/1987 | Bro | 604/66 X |
| 4,710,164 | 12/1987 | Levin et al. | 604/66 X |
| 4,718,891 | 1/1988 | Lipps | 604/66 X |
| 4,769,001 | 9/1988 | Prince | 604/4 |

FOREIGN PATENT DOCUMENTS

| | | | |
|---|---|---|---|
| 2179980 | 11/1973 | France | 61/3 |
| 8602858 | 5/1986 | PCT Int'l Appl. | 13/00 |

Primary Examiner—Richard J. Apley
Assistant Examiner—L. Thomas
Attorney, Agent, or Firm—Louis A. Morris

[57] ABSTRACT

Apparatus for withdrawing blood from a donor by means of a blood pump. The apparatus incorporates an extracorporeal system which, on the basis of donor blood pressure measurement, controls the flow rate of the blood pump in such a way that during the withdrawal procedure the pump withdraws an optimum amount of blood per unit of time from the donor.

13 Claims, 5 Drawing Sheets fig. 2

FIG. 3

$P_A$: ACTUAL DONOR PRESSURE
$P_S$: DONOR PRESSURE TARGET
=: REMAINS CONSTANT
$Q_{MAX}$: MAX. BLOOD FLOW RATE

↑ = INCREASE
↓ = DECREASE

| | BLOOD FLOW RATE Q | DONOR PRESSURE TARGET $P_S$ |
|---|---|---|
| 1. $P_A > P_S + \Delta_1$ | ↑ | = |
| 2. $P_S - \Delta_2 < P_A < P_S + \Delta_1$ WHERE $\Delta_2 = \Delta_1$ OR $\Delta_2 \neq \Delta_1$ | | |
|   a. SITUATION 3b HAS NOT YET OCCURRED BEFORE | = | ↓ $(\dot{P}_S)_1$ |
|   b. SITUATION 3b HAS OCCURRED BEFORE AND | | |
|     1. $aQ_{MAX} \leq Q \leq bQ_{MAX}$, OR | = | ↓ $(\dot{P}_S)_2$ |
|     2. $Q < aQ_{MAX}$ OR $Q > bQ_{MAX}$ a AND b BEING CONSTANTS, $a < b$ | = | ↓ $(\dot{P}_S)_3$ |
| 3. a. $P_S - \Delta_3 \leq P_A < P_S - \Delta_2$ | ↓ | = |
|   b. $P_A < P_S - \Delta_3$ WHERE $\Delta_3 > \Delta_2$ | ↓ | $+\Delta P_S$ (AFTER ATTAINING SITUATION 1) |

FIG. 4 fig.5

APPARATUS AND METHOD FOR WITHDRAWING AN OPTIMUM AMOUNT OF BLOOD PER UNIT OF TIME FROM A DONOR

BACKGROUND OF THE INVENTION

An example of an apparatus known to the art for withdrawing blood from a donor is that disclosed in PCT Patent Application 8 600 231.

The apparatus described therein is suited to be used for extracting as well as for reinfusing blood and comprises a blood pump, a pressure sensor, and a microprocessor based control system. The flow rate is optimized by sensing pressure at at least two different blood extraction rates and extrapolating the data to generate a pressure vs. flow rate limit curve. The flow rate of the blood pump is then increased to a maximum nominal flow rate of 100 ml/min provided the measured blood pressure at this maximum nominal flow rate is at least equal to the blood pressure which, according to the generated pressure versus flow rate control curve, corresponds to said maximum nominal flow rate. If at a certain flow rate Q which is smaller than the maximum nominal flow rate $Q_{max}$, the measured blood pressure attains a value which, according to the control curve, corresponds to $Q_{max}$, Q instead of $Q_{max}$ is used as the maximum allowable blood flow rate.

Although said well-known device may be used to control the amount of blood withdrawn from a donor, a major drawback to the apparatus described in PCT 8 600 231 is that the pressure vs. flow rate control curve is determined only at the outset of blood extraction, so that any donor-dependent changes in the blood supply after this initial phase will result in non-optimum blood extraction. As the known process allows for a safety margin based on the average donor, the blood extraction may exceed the vein flow capacity of the one donor and remain below that of the other. In the former situation in particular there may be problems when extracting blood.

The present invention provides an apparatus and method which permits the continuous withdrawal of an optimum amount of blood from a donor while avoiding the problems of the known devices. By optimum amount it is meant the highest rate of withdrawal of blood allowable in view of the characteristics and conditions of the donor.

SUMMARY OF THE INVENTION

The invention relates to an apparatus for withdrawing an optimum amount of blood per unit of time from a donor, which apparatus comprises
  a blood connection for connecting the apparatus to the vascular system of the donor;
  blood flow conduit means for conducting blood withdrawn from the donor by way of said blood connection;
  a blood pump connected to the blood flow conduit means for withdrawing blood from the donor through said blood flow conduit means, said pump being connected to an electric power source so as to be energized by it;
  blood flow rate measuring means cooperating with the blood pump to obtain an electric signal representing the flow rate of the blood pump;
  a pressure transducer for measuring the blood pressure PA connected to said blood flow conduit means between the blood connection and the blood pump, said pressure transducer converting the measured pressure PA into an electric signal supplied to a transducer output connection;
  a control device connected to the transducer output connection, the blood flow rate measuring means, and the electric connections of the blood pump for controlling the flow rate Q of the blood pump in response to the pressure PA measured by the pressure transducer and the blood flow rate Q.

BRIEF DESCRIPTION OF THE DRAWINGS

The invention will now be illustrated with reference to the accompanying drawings.

DETAILED DESCRIPTION OF THE INVENTION

The apparatus according to the invention is characterized in that the control device comprises means for adjusting the flow rate Q of the blood pump to a value Qm at which the change in pressure $\Delta PA$ resulting from a particular change in the flow rate $\Delta Q$ remains just below a maximum allowable value $(\Delta P_A)_m$.

At a blood extraction of up to 50 ml/min. changes in pressure due to particular changes in the flow rate will as a rule remain well below the maximum permissible value to be set. This maximum permissible value should be determined experimentally. In general, such a value will be chosen as will cause no problems even for donors having a relatively weak vascular system.

After a maximum permissible value for pressure changes due to particular changes in the flow rate has been entered into the control device, which is usually equipped with a microprocessor, the pressure is measured continuously with a pressure transducer and passed on to the control device. In it the response of the pressure to changes in the flow rate is constantly sensed. The control device will continuously control the flow rate so that the maximum permissible value or target value is just prevented from being exceeded. In this manner blood can be withdrawn from a donor at a maximum flow rate and, moreover, the donor flow rate will continuously be adjusted.

A particular embodiment of the apparatus according to the invention when no modulation is employed is characterized in that the control device is adapted to be so programmed that at the start of the withdrawal of blood from the donor ("situation 1") the flow rate is increased until the measured pressure $P_A$ falls below a preset initial value donor pressure target $P_S - \Delta_2$ ("situation 3a"), whereupon the flow rate Q is reduced until the pressure $P_A$ exceeds the value $P_S - \Delta_2$. The symbol "$\Delta$" generally represents certain pressure margins which might be selected by the operator and set in the control device in accordance with the operator's observations concerning the characteristics and condition of the donor, or which might be pre-set by the manufacturer of the apparatus.

According to a variant embodiment of the latter apparatus the control device is adapted to be so programmed that as long as the pressure $P_A$ is in the range given by $$P_S - \Delta_2 < P_A < P_S + \Delta_1 (\text{"situation 2"})$$

the prevailing blood flow rate Q is kept constant while the donor pressure target $P_S$ is reduced at a certain rate of change ($\dot{P}_S$).

A further variant embodiment is characterized in that the rate of change $\dot{P}_S$ is $(\dot{P}_S)_1$ in case "situation 2" is attained without $P_A$ having reached before a value represented by $$P_A < P_S - \Delta_3 (\text{"situation 3b"})$$

$(\dot{P}_S)_2$ in case "situation 2" is attained after $P_A$ having reached before a value represented by $$P_A < P_S - \Delta_3 (\text{"situation 3b"})$$

and, moreover, Q follows from $$aQ_{max} \leq Q \leq bQ_{max}$$

$(\dot{P}_S)_3$ if "situation 2" is attained after $P_A$ having reached a value represented by $$P_A < P_S - \Delta_3 (\text{"situation 3b"})$$

and, moreover, Q follows from $$Q < aQ_{max} \text{ or } Q > bQ_{max},$$

where $(\dot{P}_S)_1 > (\dot{P}_S)_2 > (\dot{P}_S)_3$, a and b are constants and $a < b$.

In this embodiment it is avoided that after an increase in the flow rate the measured pressure will again very rapidly drop considerably below a previously set target pressure.

Preferably, the apparatus according to the invention is further characterized in that in "situation 3b" the donor pressure target $P_S$ is increased by $\Delta P_S$ after "situation 1" has been attained. $\Delta P_S$ is a specific value which might be selected by the operator of the apparatus of the invention in accordance with the operator's observations concerning the characteristics and condition of the donor, or might be pre-set by the manufacturer of the apparatus.

This embodiment is particularly suitable in cases where the measured pressure has dropped quite considerably below a previously set target pressure. In this way it is avoided that after an increase in the flow rate the measured pressure will again drop considerably below the last target pressure set.

Alternatively, use may with advantage be made of an apparatus characterized in that it comprises a modulator between the blood connector and the blood pump, said modulator subjecting the blood flow to a periodic variation in flow rate and said control device comprising means for adjusting the blood flow rate to a value at which the amplitude of the pressure response to said periodic blood flow variation reaches a particular maximum and is maintained at or below said maximum A variant embodiment of the latter apparatus is characterized in that the blood flow conduit means comprise a flexible blood line and that the modulator comprises means for periodically compressing said blood line.

Instead of the modulator being provided somewhere between the blood connector and the blood pump, it may be accommodated in the pump itself. This more readily allows the modulation frequency to be adapted to the value of the blood flow rate.

Upstream of the modulator there is the pressure transducer, the measured signal of which is passed on to a microprocessor to establish the amplitude of said modulation. The flow rate is increased as long as the target value has not been attained. Upon reaching a particular maximum amplitude of pressure response the pumping flow rate is kept constant and it is lowered when the amplitude of pressure response exceeds such particular maximum since such maximum is the maximum allowable pressure variation.

Figure 1:
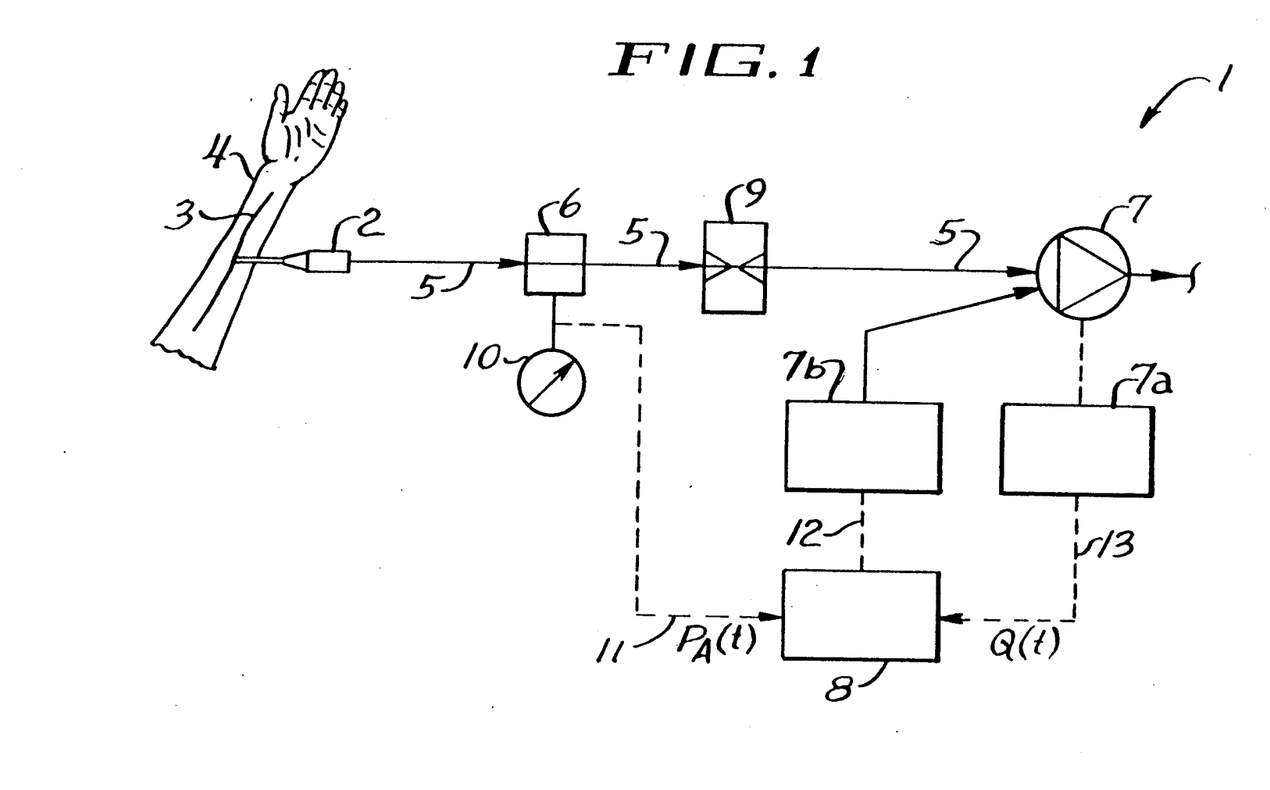
FIG. 1 shows an embodiment of an apparatus according to the invention.

The apparatus 1 depicted schematically in FIG. 1 is connected by way of a blood connection in the form of a needle 2 to a vein 3 in the arm 4 of a donor. The needle 2 is also connected to a blood line 5 forming part of the blood flow conduit means for conducting the blood withdrawn from the donor. To the blood line 5 there are further connected a pressure transducer 6 and a blood pump 7. The pressure transducer 6 has a visual display 10 for reading the actual pressure $P_A$ at the exit of the needle 2. Along a signal line 11, the transducer 6 supplies to a control device 8 an electric signal representing the pressure $P_A$. Moreover, the blood pump 7 cooperates with means 7a for measuring the blood flow rate of the pump. These blood flow rate measuring means are not shown in FIG. 1, but the electric signal representing the measured blood flow rate is supplied to the control device 8 by means of a signal line 13. Said control device serves to control the flow rate of the blood pump 7 in response to the actual values of the pressure $P_A$ and the blood flow rate Q. To that end the blood pump 7 is energized by an electric power source 7b controlled by the control device 8 as is schematically indicated by a connection 12. The control device 8 incorporates a microprocessor not shown in FIG. 1. One of the tasks of the microprocessor is to see that the control device 8 operates according to a certain control algorithm in conformity with FIG. 3, as will be explained below.

Furthermore, the apparatus according to the invention may comprise a modulator 9, which in one of the embodiments to be described alternately compresses the blood line 5 and allows it to expand again.

Figure 2:
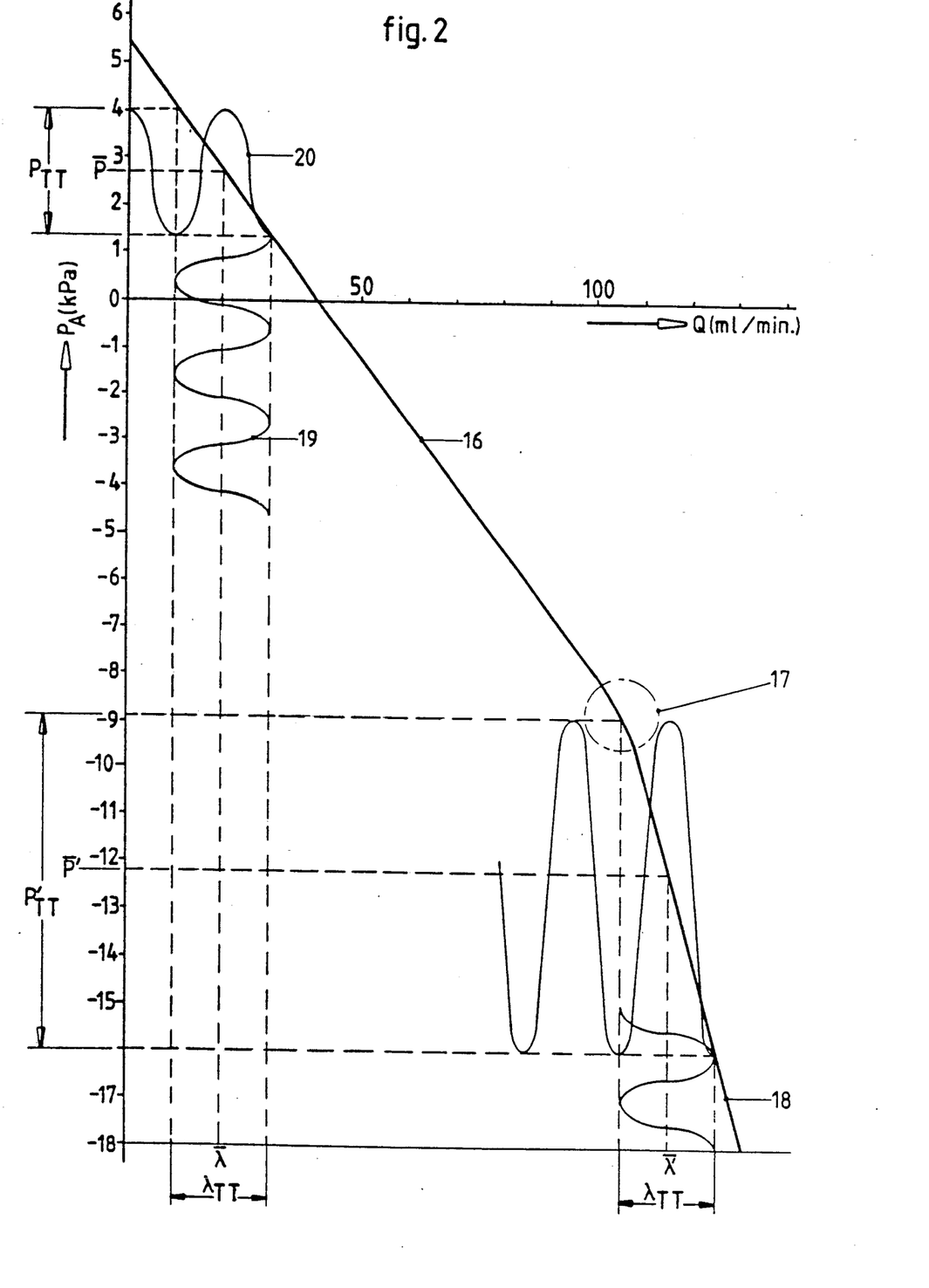
FIG. 2 illustrates a graph in which the blood pressure is represented as a function of the flow rate.

The graph of FIG. 2 shows the relation between the measured blood pressure $P_A$ in kPa (1 kPa $\approx$ 7.5 mm Hg) and the blood flow rate Q (in ml/min). It must be realized that during the blood withdrawal procedure the condition of the donor may change in an unpredictable way. Consequently, the pressure vs. flow rate curve shown in FIG. 2 only represents the $P_A/Q$-relation at a certain point in time during the blood withdrawal. The $P_A/Q$-relation not being constant but continuously changing, it is not sufficient to base the optimum blood flow rate on the condition of the donor prevailing at the start of the withdrawal procedure.

To allow for continuous changes in the pressure vs. flow rate curve the apparatus according to the invention measures the blood pressure $P_A$ either continuously or at separate instants succeeding each other at sufficiently short intervals.

Although the pressure vs. flow rate curve changes during the withdrawal procedure, it has been found that the curve maintains its general shape characterized by an initial part 16, which at a bending point 17 changes over to a steeper part 18.

As shown in FIG. 2, the curve 19 represents a sinusoidal variation of the blood flow rate (along the abscissa) as a function of time (along the ordinate). This variation is superimposed by the modulator 9 on the blood flow rate determined by the blood pump 7. The response of the measured blood pressure $P_A$ to the blood flow rate modulation 19 is shown by the curve 20. As can be seen, the sinusoidal variation of the blood flow rate is superimposed on an average blood flow rate $\bar{\lambda}$. The amplitude of this variation is $\frac{1}{2}.\lambda_{TT}$. The average value of the blood pressure response is $\bar{P}$, the amplitude of the blood pressure variation is $\frac{1}{2}.P_{TT}$.

Since the apparatus operates in the linear part 16 of the blood pressure vs. flow rate curve, the change in blood pressure in response to the sinusoidal variation of the flow rate is also sinusoidal. If the blood flow rate is increased to $\bar{\lambda}$, the same sinusoidal variation $\lambda_{TT}$ of the flow rate gives rise to a different response in blood pressure. In the first place, due to the greater steepness of the curve part 18, the magnitude of the pressure variation is much larger than in the former case, being $P'_{TT}$ instead of $P_{TT}$. Secondly, due to the bending of the pressure vs. flow rate curve at point 17, the pressure variation is no longer perfectly sinusoidal, the maximum pressure being smaller than the average pressure $\bar{P}' + \frac{1}{2}.P'_{TT}$ and the minimum pressure being lower than $\bar{P}' - \frac{1}{2}.P'_{TT}$. Consequently, it may be said that, starting from a flow rate zero, an increase in the average blood flow rate while the sinusoidal variation of Q is maintained, leads both to an increase in variation of the blood pressure and a deformation of the shape of the blood pressure variation as compared with the situation at relatively low blood flow rates.

Accordingly, there are two parameters for detecting the attainment of the bending point 17, viz. the increase in magnitude of the pressure variation and the asymmetry of the pressure curve in response to a symmetric, e.g. sinusoidal, variation of the flow rate.

By choosing a particular amplitude for the superimposed periodic flow rate variation, and allowing the variation of the pressure response ($P_{TT}$) and/or the asymmetry of the pressure response ($\bar{P}' - \frac{1}{2}.P'_{TT}$) to attain a certain maximum value ($P_{TT})_{max}$, the blood may be withdrawn from the donor at an optimum flow rate, i.e. a flow rate remaining just below a maximum allowable flow rate. ($P_{TT}$)max will be less than $P'_{TT}$ and greater than $P_{TT}$.

Figure 3:
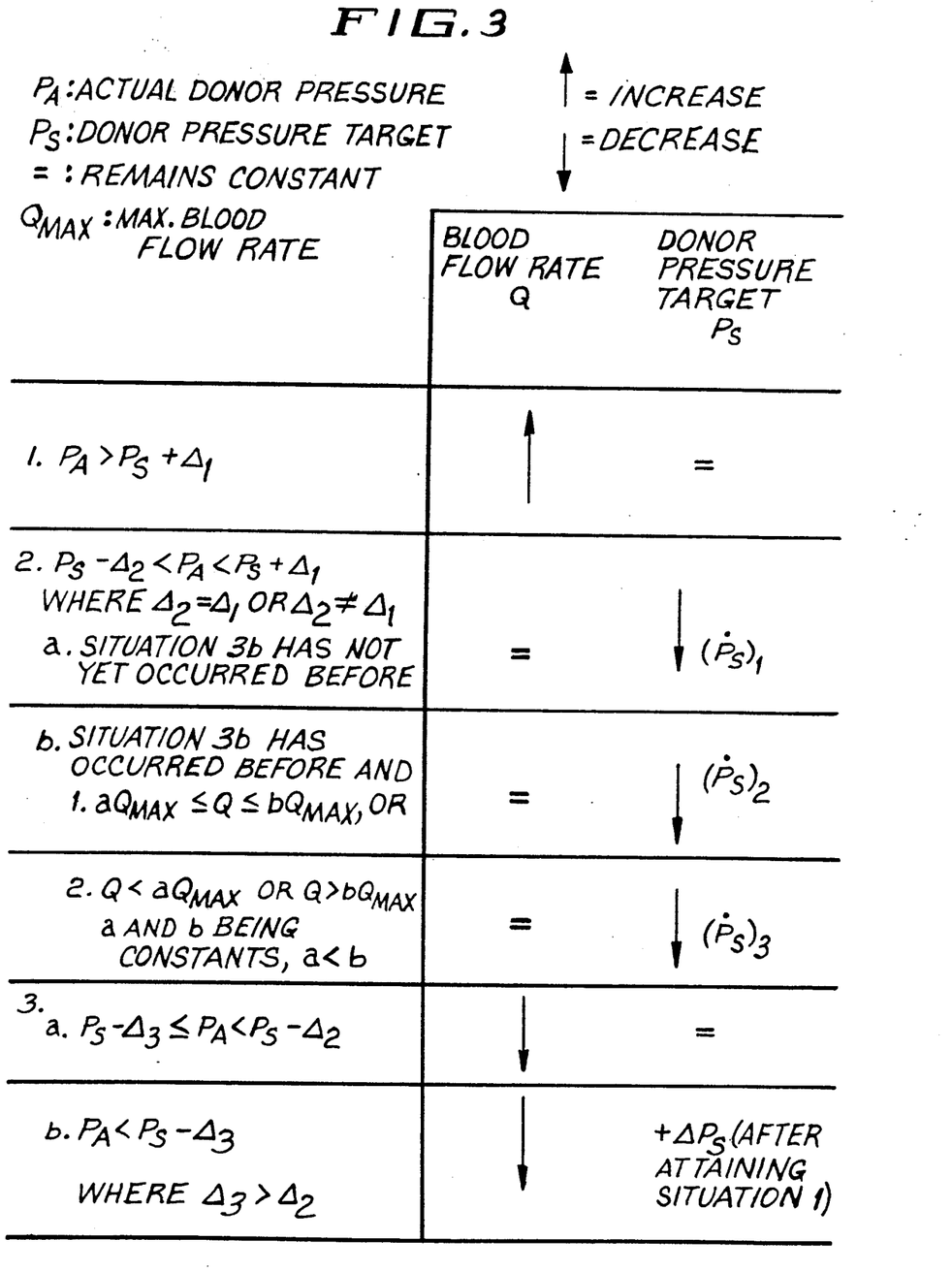
FIG. 3 is a table showing the control algorithm for an apparatus operating without a modulator.
Figure 4:
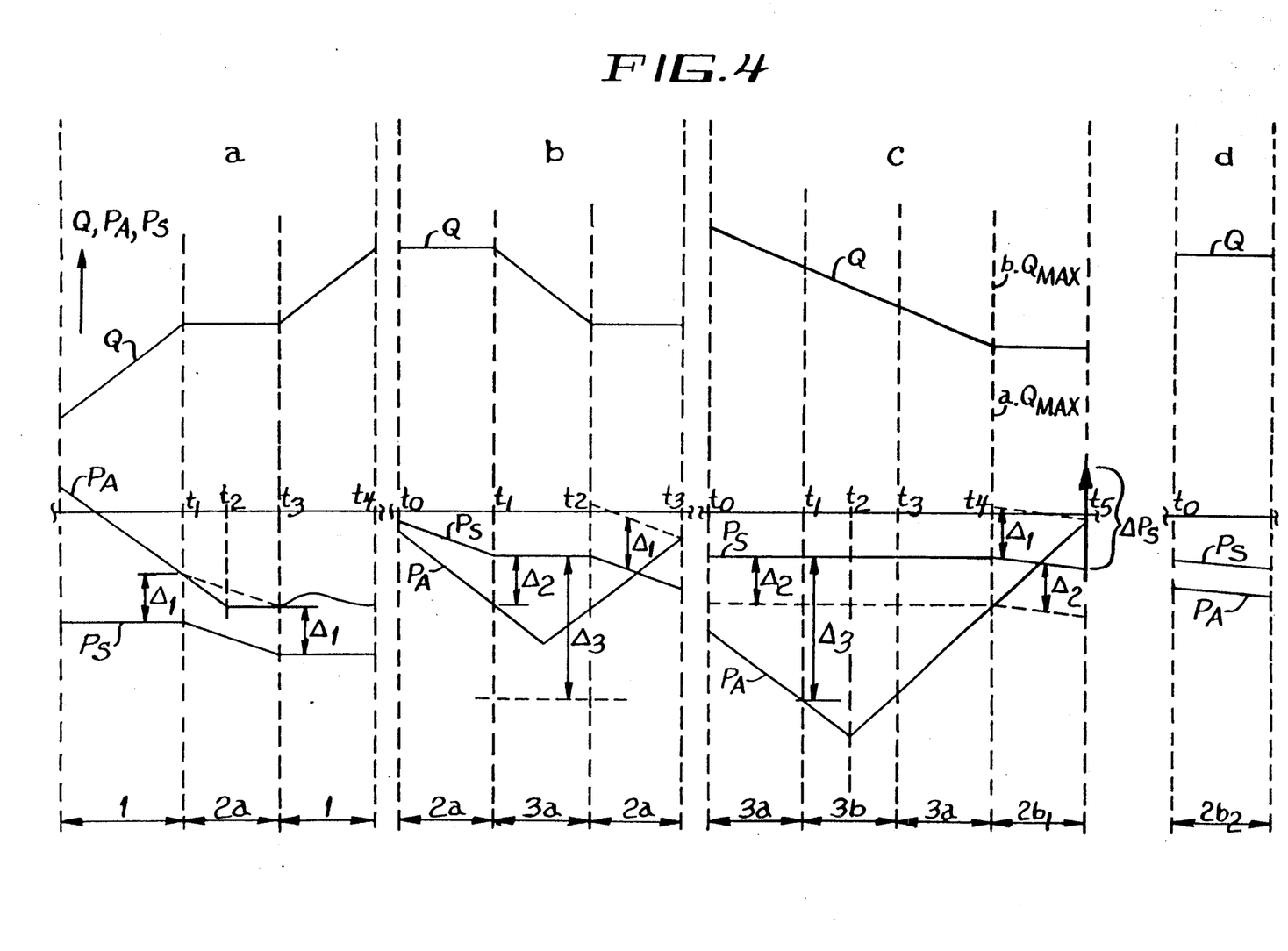
FIG. 4 depicts the measured blood flow rate Q, the blood pressure $P_A$ and the donor pressure target $P_S$ as a function of time for a particular case illustrating the control algorithm according to FIG. 3.

FIGS. 3 and 4 pertain to an embodiment of the apparatus according to the invention without the use of the modulator 9. In this case the apparatus operates according to a control algorithm represented in FIG. 3. Depending on the measured blood pressure $P_A$ the following situations may be distinguished (see also FIG. 4):
1. $P_A$ exceeds the value $P_S+\Delta_1$ ("situation 1").

In this case the blood flow rate Q is increased and the preset donor pressure target ("set point") $P_S$ remains unaltered. The increase in blood flow rate leads to a decrease of the measured blood pressure. This situation generally represents a certain pressure margin which might be selected by the operator and set at the control device 8.
2. $P_A$ is somewhere between $P_S-\Delta_2$ and $P_S+\Delta_1$ ("situation 2").

In this situation the blood flow Q is kept constant and the donor pressure target is decreased at a certain rate of change $\dot{P}_S$. Depending on the particular circumstances the following three sub-situations may be distinguished:

"Situation 2a"

This situation prevails when situation 3b (to be explained below) has not yet occurred before. In this case the rate of change of $P_S$ is $(\dot{P}_S)_1$. This situation is shown in FIG. 4a and FIG. 4b.

"Situation 2b1"

This is a case in which situation 3b has already occurred before and, moreover, one in which Q follows from $$aQ_{max} \leq Q \leq bQ_{max}$$

where $Q_{max}$ is a certain adjustable maximum value of the blood flow rate Q and a and b are constants likewise adjustable by the operator, a being smaller than b. In situation 2b1 the of change of $P_S$ is $(\dot{P}_S)_2$, which is smaller than 1. FIG. 4c shows such a situation.

"Situation 2b2"

Again, as in situation 2b1, this is a case in which situation 3b has already occurred before, but now the blood flow rate Q has a value following from $$Q < aQ_{max}, \text{ or } Q > bQ_{max}$$

In this situation exemplified by FIG. 4d, the rate of change of $P_S$ is $(\dot{P}_S)_3$. The latter is smaller than $(\dot{P}_S)_1$ and $(\dot{P}_S)_2$, so $$(\dot{P}_S)_1 > (\dot{P}_S)_2 > (\dot{P}_S)_3$$

3a. $P_A$ is at least equal to $P_S - \Delta_3$, but smaller than ("situation 3a").

In this case the blood flow rate is decreased while the prevailing donor pressure target $P_S$ is kept constant. This situation is shown in FIG. 4b and FIG. 4c.
3b. $P_A$ has dropped to a value below $P_S-\Delta_3$ ("situation 3b")

In this situation the blood flow rate is decreased and, as soon as situation 1 has been attained, the donor pressure target $P_S$ is automatically increased stepwise by a value $\Delta P_S$. FIG. 4c illustrates this situation. We will now discuss the various situations depicted in FIGS. 4a–4d.

In the situation of FIG. 4a, which may be regarded as the starting situation, $P_A$ is positive. In view of the fact that $P_A$ is larger than $P_S+\Delta_1$, the system is in situation 1. Consequently, as shown by the control algorithm of FIG. 3, the control device increases the blood flow rate. This blood flow rate increase leads to a decrease of the blood pressure $P_A$ of the donor as sensed by the transducer 6. Situation 1 is maintained by the control device 8 until $P_A$ drops below a value $P_S+\Delta_1$. At that instant the system enters into situation 2. Because situation 3b has not occurred before, the system is in situation 2a. This means that as long as the conditions for situation 2a prevail the blood flow rate is kept constant while, simultaneously, the donor pressure target $P_S$ is decreased. Assuming that for some reason the blood pressure keeps decreasing for some time and then, at time $t_2$, reaches a comparatively constant value, it will be seen that at instant $t_3$ the pressure $P_A$ again attains a value exceeding $P_S+\Delta_1$. This means that the system has now again reached situation 1 so that the blood flow rate Q is now further increased while $P_S$ is kept constant at the value obtained at time $t_3$. For one reason or another the donor blood pressure $P_A$ undergoes a short fluctuation until time $t_4$.

According to FIG. 4b the system at time $t_o$ is in a situation in which the blood flow rate Q is at a relatively high value. Due to the fact that $P_A$ is smaller than $P_S+\Delta_1$ but larger than $P_S-\Delta_2$, the system is now in situation 2a. Consequently, the blood flow rate Q is constant and the donor target $P_S$ is decreased at a certain rate of change $(\dot P_S)_1$.

At time $t_1$ the blood pressure $P_A$ drops below the value $P_S-\Delta_2$, so that the system now passes into situation 3a. This means that during a period $t_1$ to $t_2$ the blood flow rate is decreased and the donor pressure target $P_S$ kept constant. The decrease of the blood flow rate Q leads to an increase in the donor blood pressure $P_A$, so that eventually, at time $t_2$, the latter starts to exceed the value $P_S-\Delta_2$. By time $t_2$ the system has, again, reached situation 2a assuming that situation 3b has not yet occurred before. In this situation the blood flow rate is kept constant, while the donor pressure target $P_S$ is decreased at a rate of change $(\dot P_S)_1$.

According to FIG. 4c the system at time $t_o$ is in situation 3a where $P_A$ is smaller than $P_S-\Delta_2$, but larger than $P_S-\Delta_3$. Now the blood flow rate Q is decreased while the donor pressure target $P_S$ is kept constant. Assuming that for some reason the donor blood pressure keeps decreasing despite the lowering of the blood flow rate, it will, at instant $t_1$, drop below the value.

The system then changes over to situation 3b in which a further decrease of the blood flow rate Q takes place. At time $t_2$ the value $P_A$ stops decreasing, so that at time $t_3$ the donor blood pressure $P_A$ again exceeds the value $P_S-\Delta_3$, thereby bringing the system back into situation 3a. The system remains in situation 3a until at time $t_4$ the blood pressure $P_A$ has increased to such a value that it again exceeds $P_S-\Delta_2$.

As is shown in FIG. 4c, the blood flow rate Q at time $t_4$ is between the values $aQ_{max}$ and $bQ_{max}$, causing the system to change over to situation 2b1. In this situation the blood flow rate Q is not any longer decreased but kept constant at the value obtained at time $t_4$, whereas the donor pressure target $P_S$ is lowered at a rate of change $(\dot P_S)_2$. Situation 2b1 lasts until at time $t_5$ $P_A$ exceeds the value $P_S+\Delta_1$, thereby bringing the system into situation 1. As follows from the table of FIG. 3, the donor pressure target $P_S$ is then increased stepwise by a value $\Delta P_S$, because the preceding situation 3b at time $t_5$ ultimately led to situation 1.

According to FIG. 4d the blood flow rate at time to exceeds the value $b.Q_{max}$, the donor blood pressure $P_A$ being between the values $P_S+\Delta_1$ and $P_A-\Delta_2$. Consequently, the system is in situation 2b2. In this case the blood flow rate Q is kept constant while the donor pressure target is reduced at a rate of change $(\dot P_S)_3$.

The operation of the apparatus according to the invention will now be elucidated for an embodiment operating according to the control algorithm of FIG. 3, i.e. without the use of the modulator 9.

EXAMPLE 1

As part of an extracorporeal blood treatment in which blood was withdrawn from a donor, plasma being extracted therefrom by a plasmapheresis device and the remaining blood cell fraction reinfused into the donor's blood circulation, needle 2 (see FIG. 1) was connected to the vein 3 of a donor 4. The donor's blood was pumped through a blood line 5 to a pump 7. Interposed between the pump 7 and the needle 2 was a pressure transducer 6 to determine the response of the donor's blood pressure to small changes in the flow rate.

The control device 8 was capable of controlling the donor pressure target $P_S$ between $-2.7$ kPa ($-20$ mm Hg) and a preset minimum target pressure $(P_S)_{min}$ to be set between $-16.2$ and $-2.7$ kPa ($-120$ and $-20$ mm Hg).

Throughout the treatment the set donor pressure target $P_S$ was compared with the pressure $P_A$ measured by the pressure transducer 6. The first target pressure was $-2.7$ kPa ($-20$ mm Hg) set by an operator at the control device 8.

At the start of the treatment $P_A$ was always higher than the set target pressure $P_S$ of $-2.7$ kPa plus a pressure margin $\Delta_1$ of 0.27 kPa (2 mm Hg). This pressure margin $\Delta_1$ was also set by the operator at the control device 8.

So, at the start of the treatment and for some time thereafter, $P_A$ followed from $$P_A > P_S + \Delta_1 (\text{"situation 1"})$$

As will be apparent from FIG. 4a, under these conditions the blood flow rate Q was increased (at a rate of 4 ml/min/sec), whereas the donor pressure target $P_S$ was kept constant.

As soon as the measured pressure $P_A$ entered the pressure interval bounded by $P_S+\Delta_1$ and $P_S-\Delta_2$, the system changed over into another situation. The chosen pressure margins $\Delta_1$ and $\Delta_2$ being equal, so that $\Delta_1=\Delta_2=0.27$ kPa, this changeover occurred after $P_A$ had dropped to a value $P_A$ following from $$P_S = \Delta_2 < P_A < P_S + \Delta_1 (\text{"situation 2a"})$$

In this situation the flow rate was kept constant and the donor pressure target $P_S$ was decreased by the control device 8 at a rate of change $(\dot P_S)_1 = 0.4$ mm Hg per second ("situation 2a" as shown, e.g., in FIG. 4a).

Provisions were made to ensure that in the case of the blood flow rate Q having to be reduced (situations 3a, 3b), the control device 8 changed Q at a rate of change Q following from $$\dot Q = 0.1 * |P_A - P_S| * (1 + 0.2 | 10 - t)$$

where t = time during which $P_A$ is below $P_S - \Delta_2$

In this way both the magnitude of the difference between $P_A - P_S$ and the time during which $P_A$ remained below $P_S - \Delta_2$ were taken into account in restoring the donor blood pressure.

When a pressure $P_A$ was measured following from $$P_S - \Delta_3 P_A < P_S - \Delta_2 (\text{"situation 3a"})$$

the flow rate was lowered while the donor pressure target $P_S$ remained the same. The pressure margin $\Delta_3$ was set at a value of 1.6 kPa, corresponding to approx. 12 mm Hg. Situation 3a lasted until $P_A$ again reached a value following from $$P_S - \Delta_2 < P_A < P_S + \Delta_1 (\text{"situation 2"})$$

Since the system did not previously reach a situation in which the blood pressure $P_A$ had dropped below a value represented by $$P_A < P_S - \Delta_3 (\text{"situation 3b"})$$

it was now in "situation 2a" in which the blood flow rate Q was kept constant and the donor pressure target $P_S$ was decreased at a rate $(\dot{P}_S)_1$ of 0.4 mm Hg per second.

As soon as the measured value $P_A$ had decreased to a value in the range of $$P_A < P_S - \Delta_3 (\text{"situation 3b"})$$

the flow rate was lowered. Upon restoration of the donor blood pressure to a value $P_A$ according to $$P_A < P_S + \Delta_1 (\text{"situation 1"})$$

the target pressure $P_S$ was increased stepwise by an amount $\Delta P_S$ equal to 0.67 kPa (5 mm Hg).

Should the blood pressure $P_A$ again drop below a value $P_S + \Delta_1$, it will depend on the prevailing value of the blood flow rate Q to what situation the system changes over. Assuming that Q was in the range represented by $$a.Q_{max} \leqq Q \leqq b.Q_{max},$$

and considering that situation 3b had already occurred before, the system changed over to situation 2b1. The donor target pressure $P_S$ was then lowered at a rate $(\dot{P}_S)_2$ amounting to 0.2 mm Hg/sec, instead of $(\dot{P}_S)_1 = 0.4$ mm Hg/sec.

The apparatus described permitted the withdrawal of blood from donors at a continuous optimum blood flow rate of even up to above 100 ml/min.

EXAMPLE 2

Figure 5:
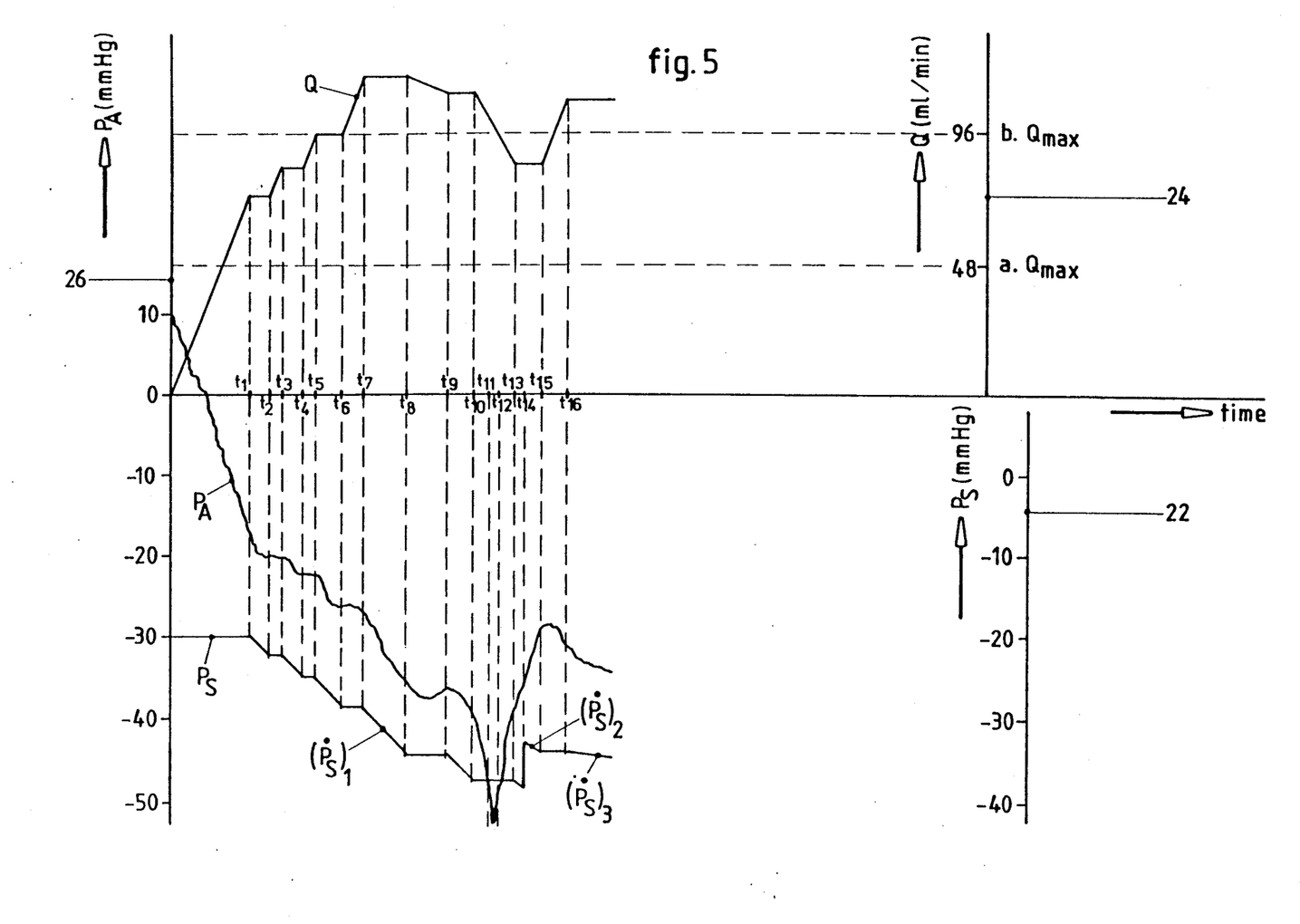

Another example is shown graphically in FIG. 5, representing the blood flow rate Q (ml/min), the actual blood donor pressure $P_A$ (in mm Hg) and the donor pressure target $P_S$ (in mm Hg) as a function of time So as to better distinguish the $P_A$ and $P_S$ graphs from each other, the $P_S$ graph has been lowered over a distance corresponding to 10 mm Hg as can be seen from the $P_S$ ordinate 22 at the bottom right side of FIG. 5. The values of the blood flow rate Q and the actual blood donor pressure $P_A$ can be found from the ordinates 24 and 26, respectively, The constants a and b and the blood flow rate $Q_{max}$ chosen were 0.4, 0.8 and 120 ml/min, respectively The pressure margins $\Delta_1$, $\Delta_2$ and $\Delta_3$ were set at 2, 2 and 12 mm Hg, respectively As can be seen, at the start of the blood withdrawal procedure the donor blood pressure $P_A$ was +10 mm Hg. The donor blood pressure target $P_S$ was initially set at $-20$ mm Hg. The conditions at the start of the withdrawal procedure were such that the system was in "situation 1" ($P_A > P_S + \Delta_1$). In accordance with the control algorithm of FIG. 3 the blood flow rate Q was increased at 4 ml/min per second while $P_S$ was kept at the value of $-20$ mm Hg. At time $t_1$ the blood pressure $P_A$ had dropped just below a value $P_S + \Delta_1 = -20 + 2 = -18$ mm Hg, resulting in "situation 2", in particular "situation 2a" ($P_S - \Delta_2 < P_A < P_S + \Delta_1$, or $-22 < P_A < -18$).

During the interval $t_1$ to $t_2$ the blood flow rate Q was kept constant while $P_S$ was decreased at a rate $(\dot{P}_S)_1 = 0.4$ mm Hg per second. Due to the decrease of PS, and Q having been kept constant, the donor blood pressure at time $t_2$ had reached a value $P_A$ exceeding $P_S + \Delta_1$ ("situation 1"). Consequently, the blood flow rate Q was further increased at a rate of change of 4 ml/min per second, the blood donor pressure target $P_S$ now remaining constant at the value it had obtained at time $t_2$. As will be apparent from FIG. 5, "situation 1" lasted until time $t_3$ when the system changed over to "situation 2a". The alternation of situations 1 and 2a continued up to time $t_8$. At that time the donor blood pressure $P_A$ had just fallen below the value $P_S - \Delta_2$, resulting in the system changing over to "situation 3a". In that situation, which lasted until time $t_9$, the blood flow rate Q was decreased so as to restore the donor blood pressure while $P_S$ was kept constant at the value obtained at time $t_8$. At about the middle of the interval $t_8$ to $t_9$ the decrease of $P_A$ had come to a halt, so that at time $t_9$ "situation 2a" was again reached "Situation 2a" lasted until time $t_{10}$, when $P_A$ had again dropped below $P_S - \Delta_2$ ("situation 3a"). In "situation 3a" the blood flow rate Q was decreased while the donor pressure target $P_S$ was maintained at the value reached at time $t_{10}$. As can be seen the donor blood pressure kept dropping despite the decrease of the blood flow rate Q, so that at time $t_{11}$ "situation 3b" was reached in which $P_A$ had fallen below a value $P_S - \Delta_3 = P_S(t_{11}) - 12$ mm Hg. Due to the continued decrease of the blood flow rate Q, at time $t_{12}$ the blood pressure $P_A$ had ultimately increased to a value exceeding $P_S - 12$ mm Hg, so that from then on the system stayed again in "situation 3a" for some time. At time $t_{13}$ the donor blood pressure had again increased to a value $P_A$ following from $P_S - \Delta_2 < P_A < P_S + \Delta_1$ ("situation 2"). Due to the fact that "situation 3b" had occurred before, the system now dwelled in "situation 2b1" ($aQ_{max} \leqq Q \leqq bQ_{max}$) during the interval $t_{13}$ to $t_{14}$ While in this interval the donor blood pressure target $P_S$ was reduced at a rate of change $(\dot{P}_S)_2 = 0.2$ mm Hg per second. At time $t_{14}$ the donor blood pressure had achieved a value $P_A$ exceeding $P_S + \Delta_1 = P_S + 2$ mm Hg ("situation 1"). Keeping in mind that "situation 3b" had occurred before, the donor blood pressure target $P_S$ was at time $t_{14}$ increased stepwise by an amount $\Delta P_S = 5$ mm Hg. Starting at time $t_{14}$ the system briefly dwelled in "situation 1", in which the blood flow rate Q was increased while the donor pressure target $P_S$ was kept constant Due to the very short time "situation 1" prevailed, the increase of Q is not discernible in FIG. 5. The system re-entering "situation 2b1" shortly after time $t_{14}$, the blood flow rate Q was again kept constant for some time while the donor pressure target $P_S$ continued to decrease at a rate of change $(\dot{P}_S)_2 = 0.2$ mm Hg per second. At time $t_{15}$ the donor blood pressure $P_A$ had increased to a value just exceeding $P_S + \Delta_1$ ("situation 1"). Consequently, from that time on the blood flow rate Q was again increased while the donor blood pressure target $P_S$ remained at the value it had obtained at time $t_{15}$. The increase in blood flow rate Q led to a decrease in the donor blood pressure $P_A$. At time $t_{16}$ the pressure $P_A$ had dropped below $P_S + \Delta_1$, so that the system changed over to "situation 2". In view of the fact that at time $t_{16}$ the blood flow rate Q had increased to a value exceeding $bQ_{max}$, the system was in "situation 2b2" as from time $t_{16}$. From this time on the blood flow rate Q was kept constant, whereas the donor blood pressure target $P_S$ was now reduced at a rate of change $(\dot{P}_S)_3 = 0.05$ mm Hg per second.

What is claimed is:

1. An apparatus for withdrawing an optimum amount of blood (Qo) per unit of time from a donor comprising:
   a. a blood connection means for connecting the apparatus to the vascular system of the donor having an inlet open to said vascular system and an outlet;

b. blood flow conduit means for conducting blood withdrawn from the donor by way of said blood connection means, having an inlet connected to said outlet of said blood connection means and an outlet;

c. a blood pump connected to the outlet of said blood flow conduit means for withdrawing blood from the donor through said blood flow conduit means, said pump being connected to a power source so as to be energized by it;

d. blood flow rate (Q) measuring means cooperating with said blood pump to obtain an electric signal representing the flow rate of blood through said blood pump which is supplied to a flow rate output connection;

e. a pressure transducer for measuring the blood pressure ($P_A$), connected to said blood flow conduit means between said blood connection means and said blood pump, said pressure transducer converting $P_A$ into an electric signal supplied to a transducer output connection;

f. a control device connected to said transducer output connection, said blood flow rate measuring means output connection, and said power source of said blood pump for controlling Q through said blood pump in response to $P_A$ and Q, wherein said control device comprises means for adjusting Q through said blood pump to Qo at which the change in pressure ($\Delta P_A$) resulting from a particular change in the flow rate remains less than a maximum allowable value $(\Delta P_A)_m$.

2. The apparatus of claim 1 wherein said control device is adapted to be so programmed that at the start of the withdrawal of blood from the donor ("situation 1") the flow rate is increased until $P_A$ ultimately falls below a preset initial value of donor pressure target $(P_S) - \Delta_2$ ("situation 3a"), where $\Delta_2$ is a suitable pressure margin constant, whereupon Q is reduced until $P_A$ exceeds the value $P_S - \Delta_2$.

3. The apparatus of claim 2 wherein said control device is adapted to be so programmed that as long as $P_A$ is in the range represented by $$P_S - \Delta_2 < P_A < P_S + \Delta_1 \text{ ("situation 2")}$$

where $\Delta_1$ is a further suitable pressure margin constant, the prevailing Q is kept constant while $P_S$ is reduced at a certain rate of change ($P_S$).

4. The apparatus of claim 3 wherein $P_S$ is
a. $(P_S)_1$ if "situation 2" is attained without $P_A$ having first reached a value represented by $P_A < P_S - \Delta_3$ ("situation 3b"), wherein $\Delta_3$ is a further suitable pressure margin constant, b. $(P_S)_2$ if "situation 2" is attained after $P_A$ having earlier reached a value represented by $$P_A < P_S - \Delta_3 \text{ ("situation 3b")}$$

and if, $$aQ_{max} \leq Q \leq bQ_{max}$$

wherein $Q_{max}$ is the maximum blood flow rate.

c. $(P_S)_3$ if "situation 2" is attained after $P_A$ having earlier reached a value represented by $$P_A < P_S - \Delta_3 \text{ ("situation 3b")}$$

and $$Q < aQ_{max} \text{ or } Q > bQ_{max},$$

where $(P_S)_1 > (P_S)_2 > (P_S)_3$, a and b are constants and a < b.

5. The apparatus of claim 4 wherein in "situation 3b" $P_S$ is increased by $\Delta P_S$ after "situation 1" has been attained, where $\Delta P_S$ is a constant.

6. The apparatus of claim 1 further including a modulating means through which the blood flow passes between said blood connection means and said blood pump, said modulating means subjecting the blood flow to a periodic variation in flow rate and said control device comprising means for adjusting the blood flow rate to a value at which the amplitude of the pressure response to said periodic blood flow variation reaches a particular maximum and is maintained at or below said maximum.

7. The apparatus of claim 6 wherein said blood flow conduit means comprises a flexible blood line and that the modulating means comprises means for periodically compressing said blood line.

8. A method for withdrawing an optimum amount of blood per unit of time from a donor comprising:
a) passing blood from the vascular system of the donor through blood withdrawal means; and
b) adjusting the flow rate of blood Q through said blood withdrawal means to a value at which the change in pressure ($\Delta P_A$) of the blood being withdrawn from the donor resulting from a particular change in the flow rate remains just below a maximum allowable value.

9. The method of claim 8 wherein at the start of the withdrawal of blood from the donor ("situation 1") the flow rate is increased until the measured pressure ($P_A$) ultimately falls below a preset initial value of donor pressure target $(P_S) - \Delta_2$ ("situation 3a"), where $\Delta_2$ is a suitable pressure margin constant, whereupon Q is reduced until $P_A$ exceeds the value $P_S - \Delta_2$.

10. The method of claim 9 wherein as long as $P_A$ is in the range represented by $$P_S - \Delta_2 < P_A < P_S + \Delta_1 \text{ ("situation 2")}$$

where $\Delta_1$ is a further suitable pressure margin constant, the prevailing Q is kept constant while $P_S$ is reduced at a certain rate of change ($P_S$).

11. The method of claim 10 wherein $P_S$ is
a. $(P_S)_1$ if "situation 2" is attained without $P_A$ having first reached a value represented by $$P_A < P_S - \Delta_3 \text{ ("situation 3b")},$$

where $\Delta_3$ is a further suitable pressure margin constant,
b. $(P_S)_2$ if "situation 2" is attained after $P_A$ having earlier reached a value represented by $$P_A < P_S - \Delta_3 \text{ ("situation 3b")}$$

and if, $$aQ_{max} \leq Q \leq bQ_{max}$$

where $Q_{max}$ is the maximum blood flow rate
c. $(P_S)_3$ if "situation 2" is attained after $P_A$ earlier reached a value represented by $$P_A < P_S - \Delta_3 \text{ ("situation 3b")}$$

and $$Q < aQ_{max} \text{ or } Q > bQ_{max},$$

where $(P_S)_1 > (P_S)_2 > (P_S)_3$, a and b are constants and $a < b$.

12. The method of claim 11 wherein in "situation 3b" $P_S$ is increased by the constant $\Delta P_S$ after "situation 1" has been attained.

13. The method of claim 8 wherein the blood flow rate is modulated to a periodic variation and the blood flow rate is adjusted to a value at which the amplitude of the pressure response to said periodic blood flow modification reaches a particular maximum and is maintained at or below said maximum.

* * * * *